United States Patent [19]

Manes

[11] Patent Number: 4,848,335
[45] Date of Patent: Jul. 18, 1989

[54] RETURN ELECTRODE CONTACT MONITOR

[75] Inventor: Michael R. Manes, Littleton, Colo.

[73] Assignee: Aspen Laboratories, Inc., Greenwood Village, Colo.

[21] Appl. No.: 156,540

[22] Filed: Feb. 16, 1988

[51] Int. Cl.⁴ ............................................. A61B 17/39
[52] U.S. Cl. ................................ 128/303.13; 128/908
[58] Field of Search ...................... 128/303.13, 303.14, 128/303.17, 908

[56] References Cited

U.S. PATENT DOCUMENTS

| 3,933,157 | 1/1976 | Bjurwill et al. | 128/303.14 |
| 4,416,276 | 11/1983 | Newton et al. | 128/303.13 |
| 4,416,277 | 11/1983 | Newton et al. | 128/303.13 |
| 4,569,345 | 2/1986 | Manes | 128/303.14 |
| 4,574,801 | 3/1986 | Manes | 128/303.14 |
| 4,617,927 | 10/1986 | Manes | 128/303.14 |

FOREIGN PATENT DOCUMENTS

| 1139927 | 11/1962 | Fed. Rep. of Germany | 128/303.13 |
| 2146534 | 4/1985 | United Kingdom | 128/303.13 |

Primary Examiner—Lee S. Cohen
Attorney, Agent, or Firm—Fields, Lewis, Pittenger & Rost

[57] ABSTRACT

Apparatus for monitoring the resistance of the return part of the patient circuit of either a dual foil or single foil return electrode according to a user's selection is disclosed. The apparatus measures the quality of the contact between the return electrode and the patient. A DC or AC converter provides a substantially DC voltage at its input that varies in relation to the resistance of the return part of the patient circuit at its AC output. Preferably, a constant current fed sinusoidal oscillator with a low pass filter at its DC output provides a substantially DC voltage related to the resistance at its AC input. An analog to digital converter converts the substantially DC voltage to a corresponding binary digital signal that is input to a programmed microprocessor. A manually operable set point switch coupled to the microprocessor is acatuated by the user which actuation establishes a resistance level with the pad (return electrode) in place on the patient. The microprocessor establishes preselected range between fixed maximum and minimum resistance values beyond which an alarm output is produced and establishes a threshold resistance value whereby upon a preselected fixed deviation, such as when the patient pad is partially detached, an alarm is produced and further an output so the RF power source will longer apply power to the active electrode.

17 Claims, 7 Drawing Sheets

RETURN ELECTRODE CONTACT MONITOR

TECHNICAL FIELD

This invention generally relates to electrosurgical apparatus and more particularly to a novel and improved return electrode monitor for electrosurgical apparatus.

BACKGROUND ART

Electrosurgical apparatus which produces high frequency currents for cutting tissue and the coagulation of small blood vessels in electrosurgery are well known.

Recent examples of such apparatus are found in U.S. Pat. Nos. 4,569,345, 4,574,801 and 4,617,927.

Certain conditions of the return electrode may result in a burn to the patient. Some attempts have been made to monitor the return electrode to avoid injury to the patient. The disclosure of U.S. Pat. Nos. 4,416,276 and 4,416,277 to Newton et al. are directed to monitoring the return electrode to insure the return electrode is in place and to avoid injury to the patient.

The monitoring approach taken by Newton et al. is to use a voltage divider and a synchronous detector along with an automatic rather than a manual operation. Newton et al. automatically interprets a safe resistance representative of safe pad contact as the lowest resistance value observed over some period of time and automatically sets the upper limit of resistance as a function of that value. The disadvantage of this approach is that the circuit is more complex and therefore more costly and is less safe than a manual operation. An automatic operation does not allow the user which is typically the clinical staff to register concurrence that the pad has been properly applied. Moreover, this disclosure does not provide a display of the measured resistance.

DISCLOSURE OF THE INVENTION

A return electrode contact monitor includes a DC to AC converter providing a substantially DC voltage at its DC input that varies in relation to a resistance at its AC output. The resistance being monitored is the resistance of the return part of the patient circuit which is coupled to the output of the DC to AC converter via a high-isolation transformer to isolate the monitor from RF voltages in the patient circuit during surgical operations. A preferred DC to AC converter is a constant current fed high-efficiency sinusoidal oscillator. An analog to digital converter converts the substantially DC voltage to a corresponding binary digital signal that is input to a programmed microprocessor. The microprocessor is responsive to a manually operable set point switch, selected activation requests and can be set for either a single or dual foil mode. The microprocessor establishes preselected fixed maximum and minimum resistance value limits beyond which an alarm output is produced as well as a threshold so that upon a preselected fixed deviation of the resistance beyond a resistance value at the instant of the last selected set point switch activation an alarm output is produced. The microprocessor produces an output to turn off the RF power source each time an alarm output is produced.

DETAILED DESCRIPTION

Figure 1A:
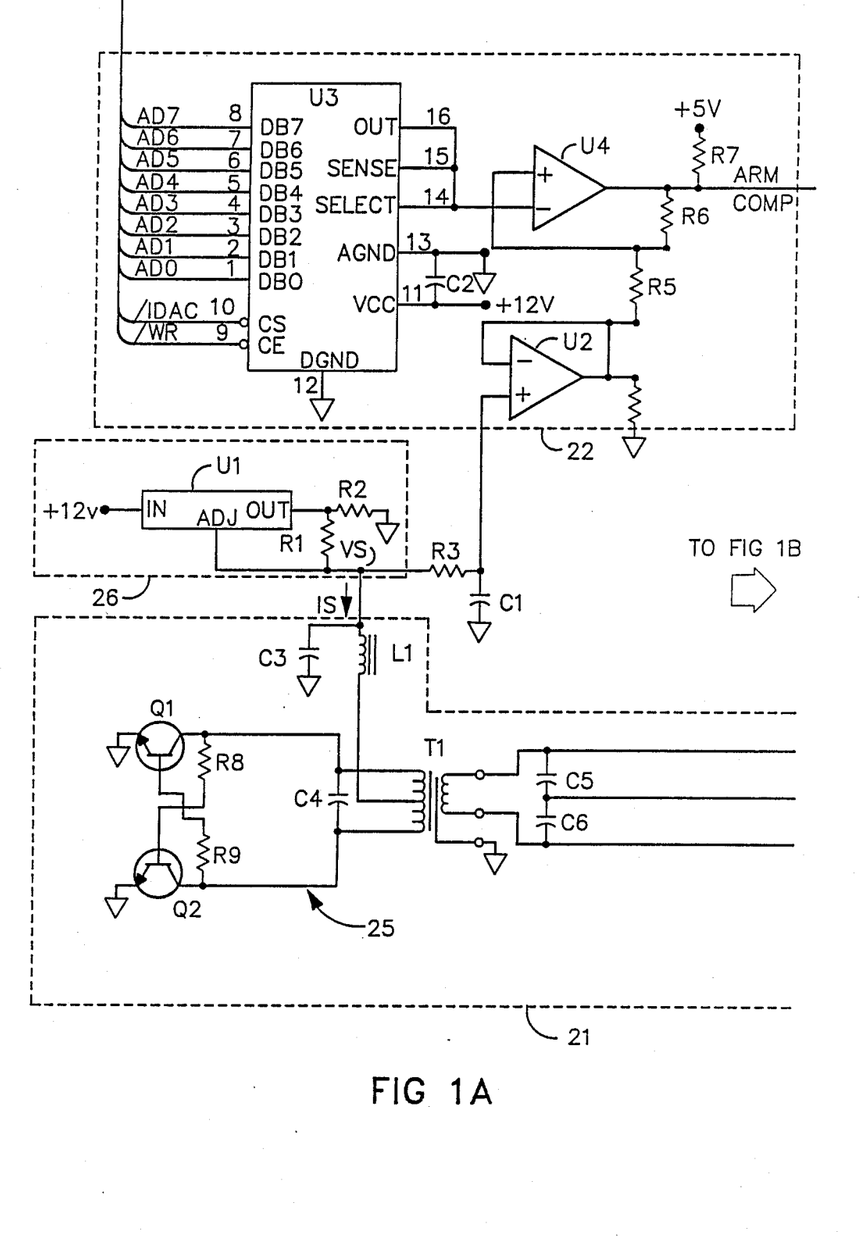
FIGS. 1A and 1B are a circuit diagram of a return electrode monitor embodying features of the present invention with a dual foil return electrode in the patient circuit.
Figures 1B, 2:
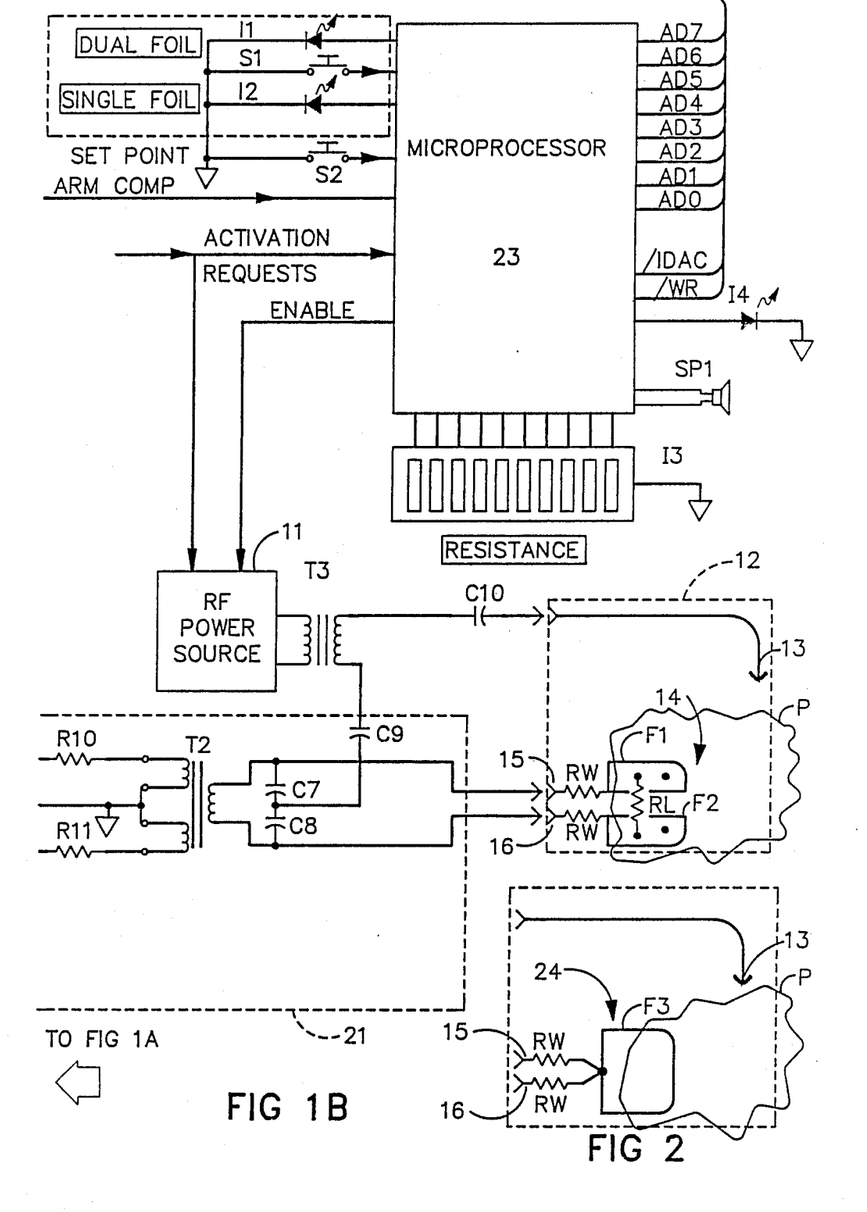
FIG. 2 is a schematic diagram of the single foil return electrode.

Referring now to FIGS. 1A and 1B of the drawing, there is shown monopolar electrosurgical apparatus which includes a conventional RF power source 11 having its output coupled by a transformer T3 to a patient circuit 12. The patient circuit 12 shown in FIG. 1B has the active electrode 13 connected to the secondary winding of the transformer T3 via a capacitor C10. A dual foil return electrode 14 shown in the patient circuit includes two foils F1 and F2 that are in contact with patient P through which the electrosurgical current passes during surgical operations. The resistance across coupling terminals 15 and 16 is the resistance of RL plus both RW's. RL represents the resistance of the tissue of patient P connected between the dual foils F1 and F2. Foils F1 and F2 are shown connected via wire resistances RW to coupling terminals 15 and 16, respectively. Wire resistances RW are generally small in relation to RL and for purposes of analysis can be ignored. The resistance of the return part of the patient circuit through which monitoring current flows is RL plus both RW's and this is the resistance across terminals 15 and 16 that is monitored for the dual foil return electrode of FIG. 1. The circuit through which the electrosurgical current flows during surgical operations includes active electrode 13, the patient, foils F1 and F2, resistors RW, capacitors C7 and C8 connected across the connecting terminals 15 and 16, a capacitor C9 connected to a common connection of capacitors C7 and C8, the secondary winding of transformer T3, and capacitor C10.

The single foil return electrode 24 shown in FIG. 2 consists of a single foil F3 having a patient P in contact therewith together with two wire resistances RW between the foil and connecting terminals 15 and 16.

The resistance of the return part of the patient circuit for the single foil return electrode 24 is the resistance of both resistances RW. A patient plate fault condition and alarm output is produced when the resistance rises above the fixed minimum MRMIN for the dual-foil mode of operation described more fully hereinafter. The terms return electrode, pad, and plate as used herein are the element that comes into contact with the patient and are synonymous.

The return electrode contact monitor of the present invention, generally stated, measures the quality of the contact between the return electrode and the patient. More specifically, the return electrode contact monitor, generally stated, includes a DC to AC converter 21 coupled to the return electrode 14 via an isolation transformer T2, an analog to digital converter 22 converting the output of the converter 21 to a corresponding binary digital signal and a programmed microprocessor 25 that receives the binary digital signal, other selected inputs and controls the output of RF power source 11 to the active electrode 13, and provides other selected outputs described hereafter.

The converter 21 shown includes a push-pull sine wave oscillator 25 and a low pass filter inclusive of inductor L1 and capacitor C3 between the output of the oscillator and the output of a constant current source 26. The oscillator is powered by constant current source 26. The oscillator includes transistors Q1 and Q2 having emitters connected to ground. A resistor R8 connects from the base of transistor Q2 to one side of the primary winding of transformer T1. A resistor R9 connects from the base of transistor Q1 to the other side of the primary winding of transformer T1. The collector of transistor Q2 connects to the common side of resistor R9 and the primary winding of transformer T1. A capacitor C4 is connected across the primary winding of transformer T1. A center tap of the primary of transformer T1 connects through the low pass filter of an inductor L1 and capacitor C3 to a voltage terminal VS which is the DC input of converter 21.

An isolation transformer T2 has a primary winding connected through resistors R10 and R11 across the secondary winding of transformer T1. The center of the primary winding of transformer T2 is connected to ground. A capacitor C5 connects from one side of the secondary winding of T1 and ground and a capacitor C6 connects from the other side of the secondary winding of T1 and ground. The secondary winding of the isolation transformer is connected to the return pad terminals 15 and 16 of the patient circuit. Resistors R10 and R11 serve to establish a minimum resistance appearing across the output of transformer T1. These resistors allow the oscillator to continue operating at close to the normal operating frequency despite a short circuit at the pad terminals 15 and 16.

The constant current source 26 includes an adjustable voltage regulator U1 which in conjunction with resistor R1 will deliver a substantially constant direct current designated IS. A resistor R2 is connected between the output of U1 and ground and serves to absorb the minimum load current from regulator U1 which exceeds the desired value for current IS. The constant current, IS, supplied by source 26, powers the oscillator via the filter inductor L1. The purpose of filter C3, L1 is to hold IS steady over the full cycle of oscillation of the oscillator 25 despite oscillatory voltage variations on the center tap of transformer T1.

Figure 6:
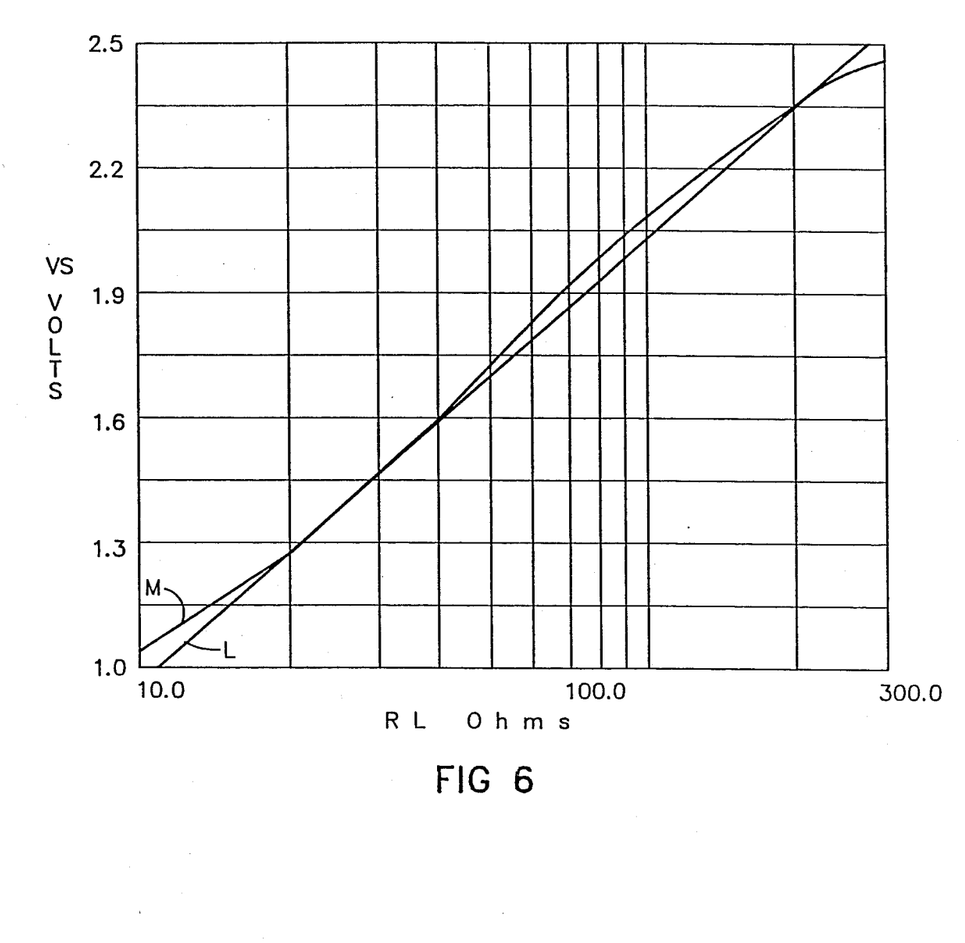
FIG. 6 is a graph showing the relationship of resistance and the substantially DC voltage produced by the DC to AC converter.
Figure 7A:
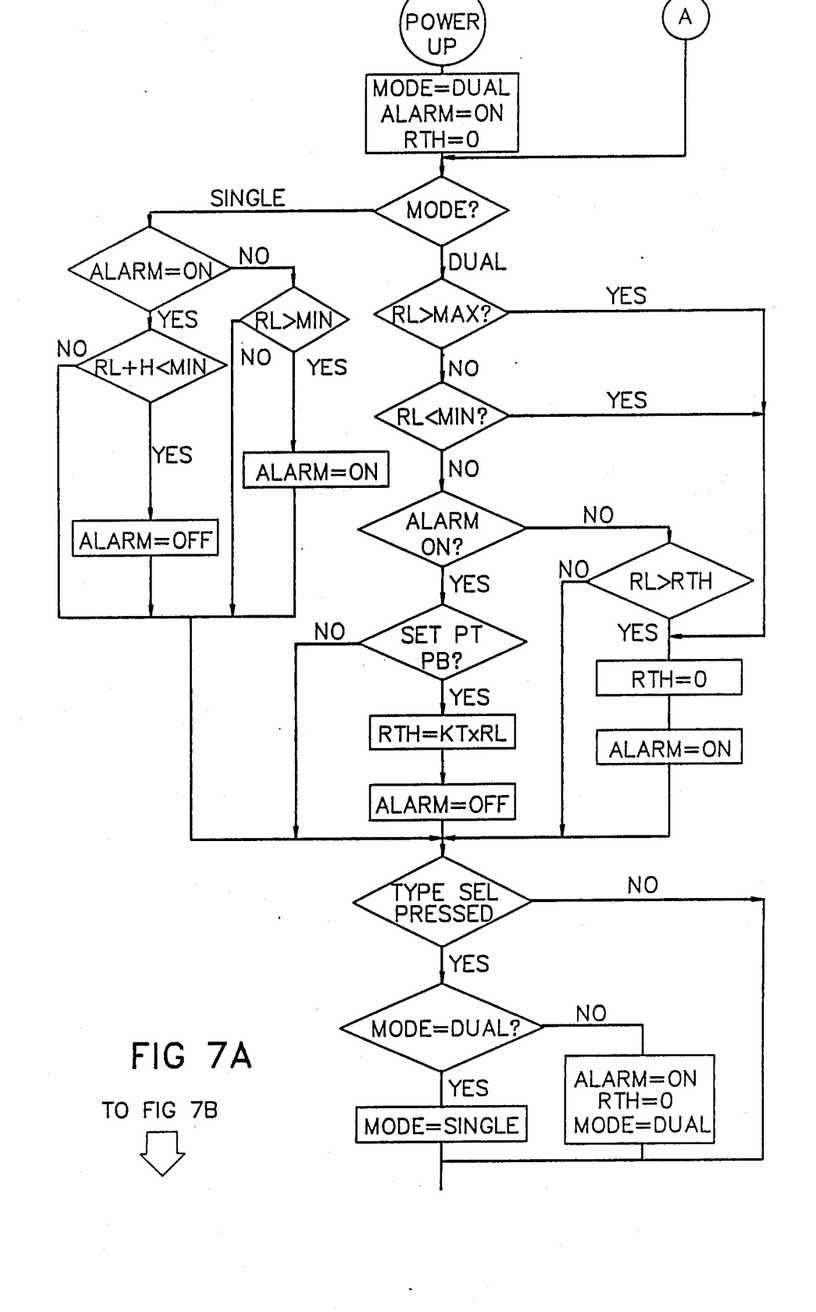
FIGS. 7A and 7B are a flow chart of the program for the microprocessor of FIG. 1B.
Figure 7B:
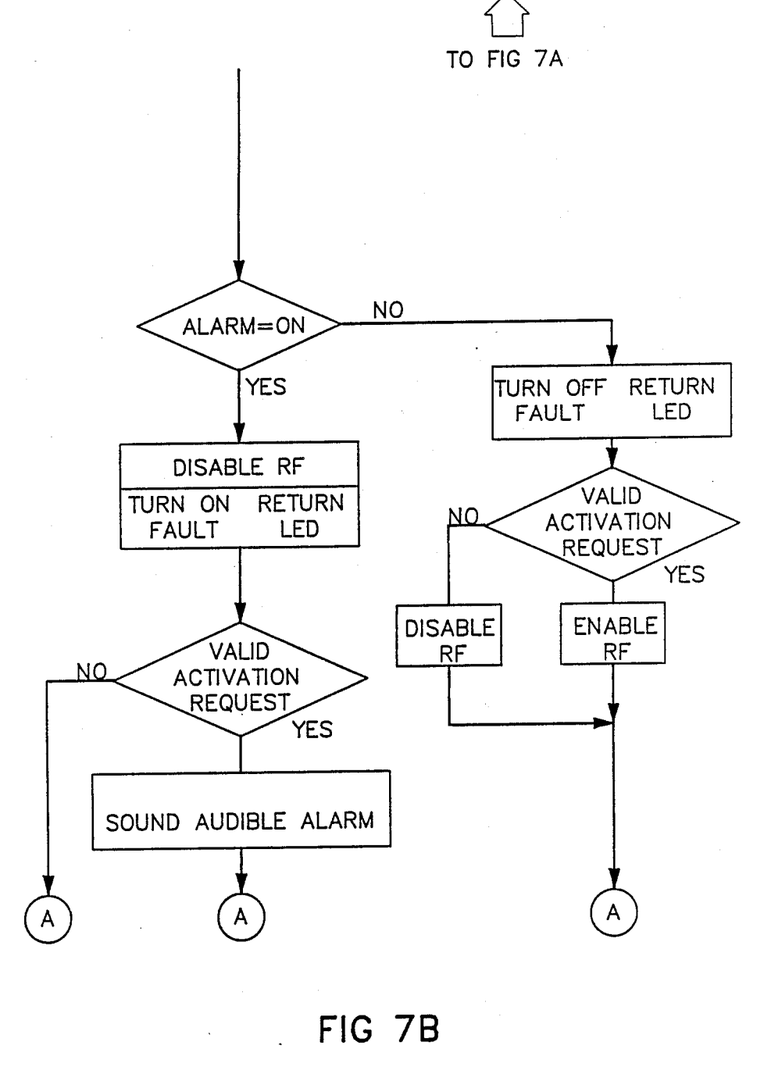

Referring now to FIG. 6 there is shown a plot of VS of converter 21 and the resistance RL across terminals 15 and 16 on a logarithm graph. Curve M is the actual plot and curve L is the ideal plot which is a straight line. This plot shows that the VS varies in a substantially logarithmic relationship with the return resistance of the patient circuit when the DC input current of converter 21 is constant.

Figure 3:
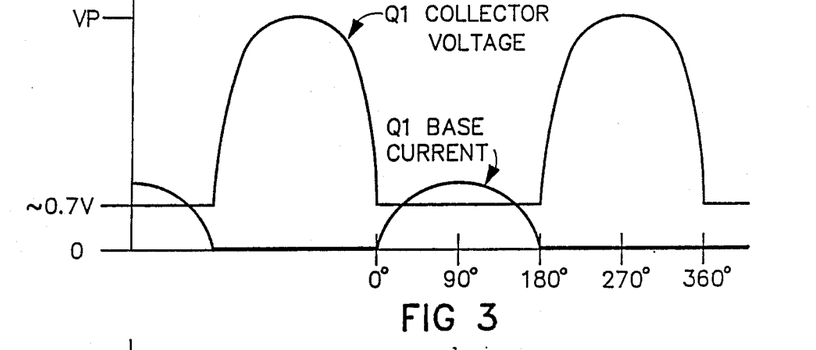
FIG. 3 is a graph showing the voltage and current waveforms for transistor Q1.

In further explanation of the operation of oscillator 25 and with particular reference to FIG. 3, on startup, both transistors Q1 and Q2 will be turned off, and current IS will flow in nearly equal proportions through resistors R8 and R9 into the bases of transistors Q1 and Q2. Because of unavoidable thermal noise and differences in gain, one of the two transistors will begin to conduct collector current more heavily than the other. Say, for example, that Q1 begins conducting more heavily than Q2. The collector voltage of Q1 will be lower than Q2's, so more base current will flow through R9 than through R8. This will cause Q1 to conduct even more heavily and Q2 will be turned off due to lack of base current. Now substantially all of current IS will flow in Q1's collector, whose voltage will be quite low, and the collector voltage on Q2 will rise unimpeded by collector current. Some of IS supplies the base of Q1.

Figure 4:
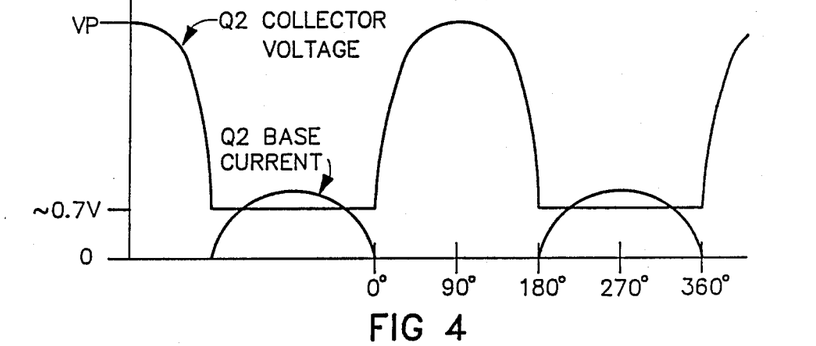
FIG. 4 is a graph showing the voltage and current waveforms for transistor Q2.

Capacitors C5 and C6 may be thought of as being transformed to a single capacitor in parallel with C4, forming a parallel resonant LC circuit with the primary magnetizing inductance of transformer T1. Since T1 has a high Q, the voltage on the primary winding of T1 is forced to take on a nearly pure sinusoidal waveshape, gaining its energy from IS. The dominant Q-limiting mechanism is the base resistors R8 and R9. This forces the collector voltage on Q2 to take the form of the positive half-cycle of a sine wave, rising to a peak value VP after 90 degrees and falling toward zero approaching 180 degrees. Since Q1 draws its base current from Q2's collector voltage, Q1 will cease to conduct when Q2's collector voltage falls below Q1's base-emitter forward voltage of about 0.7 V. Because the primary tank will sustain the sine wave and L1 will sustain current IS, Q1's collector voltage will begin to rise, and Q2 will now turn on, robbing Q1 of any base current. The second half-cycle will now continue, with Q1 and Q2's roles reversed. The voltage amplitude of the primary circuit oscillation will progressively rise from cycle to cycle until current IS is only just adequate to sustain the power losses in the oscillator circuit and that in any resistance appearing at the secondary winding of transformer T2.

Figure 5:
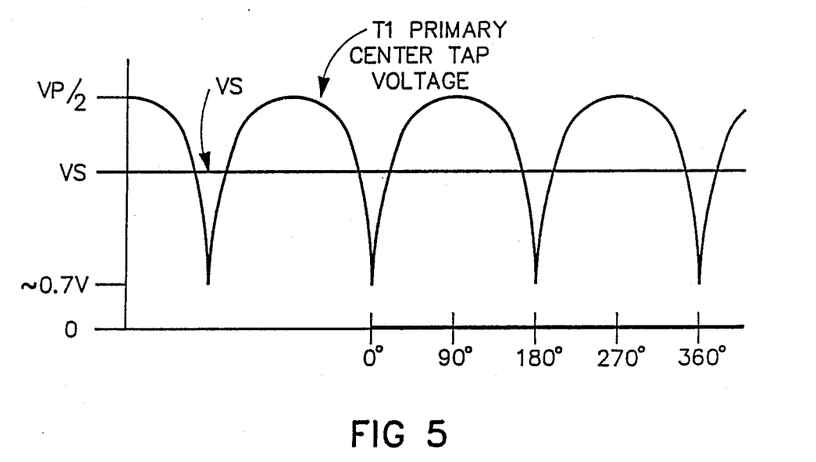
FIG. 5 is a graph showing voltage and current waveforms of the oscillator shown in FIG. 1A.

The voltage waveform appearing at the center-tap of the primary winding of transformer T1 will take the form of a full-wave rectified sinewave with a peak amplitude of VP/2, since Q1 and Q2 collectors are essentially grounded on alternate half-cycles. The DC component of such a signal is 2/Pi or about 0.637 times the peak voltage of the waveform. Because inductor L1 exhibits negligible DC impedance, the DC value of VS will be identical to that of T1. But L1 also exhibits a high impedance at the frequency of oscillation, and C3 exhibits a low reactance, so voltage VS will appear as a nearly pure or a substantially DC voltage. Thus VS will vary in direct proportion to the amplitude of the AC voltage on T1 primary, plus an offset of about 0.7 volts due to the forward base-emitter voltage of the transistors.

Any resistive components appearing in parallel with the filter L1, C3 on T1 primary will extract energy from that circuit, causing a drop in the amplitude of the primary AC voltage. This will be reflected as a corresponding drop in VS; if that resistance were to rise, VS would thus rise accordingly. The most significant of those resistive components is RL which is reflected to T1 primary by the inverse square of the product of the turns ratios of T1 and T2. Transformers T1 and T2 may be considered as a single device for purposes of analysis, but their roles are distinct. Transformer T1 serves as a high Q magnetically coupled tuned circuit acting in conjunction with C7 and C8. Transformer T2 serves to isolate the monitor circuitry and specifically the oscillator from the high RF voltages which are applied to the patient circuit and specifically through active electrode 13 during electrosurgery. For the dual foil mode the current splits so that half flows through each of capacitors C7 and C8. Capacitors C9 and C10 serve to minimize low frequency components of the electrosurgical current.

In a preferred embodiment, T1 comprises a TDK H6B RM8A400 core wound with a 79-turn bifilar pair of #32AWG magnet wire for the primary and an 18-turn #22AWG secondary. A copper Faraday shield is interposed between the two windings to minimize the effects of electrosurgical output voltages on the operation of the monitor circuit.

A low-pass filter is formed by resistor R3 and capacitor C1 to further attenuate any high-frequency noise components or voltage appearing on VS. An operational amplifier U2 serves as a high-input-impedance buffer, preventing the comparator circuitry from absorbing a portion of IS and thus inducing errors in voltage VS. An 8-bit digital-to-analog converter U3 is driven by the microprocessor. Converter U3 generates a DC output voltage in response to data transferred over data bus represented by lines ADO-AD7 when control lines /IDAC and /WR are activated. The output voltage of U3 is compared to the buffered VS by a comparator U4, which incorporates a small amount (about 5mV) of hysteresis on the voltage VS.

The microprocessor 23 executes a conventional successive approximation algorithm to determine a digital representation of the actual value of voltage VS. The microprocessor 23 is programmed to establish a range of resistance between preselected fixed maximum and minimum resistance value limits, RMAX and RMIN, beyond which an alarm output is produced. The microprocessor is further programmed to establish a preselected threshold value of resistance RTH whereby upon a preselected deviation of the resistance value at the instant of the last selected set point switch activation an alarm output is produced.

Push-button switch S1 coupled to the microprocessor allows the user to select between dual-foil and single-foil return electrode modes. The selection is displayed by illumination of either LED I1 or I2. When dual-foil operation is selected, bar graph LED display I3 is driven by the microprocessor to indicate the measured resistance. Resistances below the predetermined minimum RMIN result in illumination of none of the LED bars in I3, while resistances exceeding the maximum RMAX result in illumination of all bars. Intermediate resistances are displayed as progressive illumination of I3 bars from left to right as resistance rises from the minimum to the maximum of the range.

In dual-foil operation, the set point switch S2 is pressed by the user to register satisfactory pad placement. These activations are ignored if the pad resistance lies outside the allowed range or if single-foil mode is selected.

LED I4 is illuminated by the microprocessor whenever a patient plate fault condition is detected which results in an alarm output. That condition is defined as:

In single-foil mode, detected resistance in excess of the allowed minimum RMIN for dual-foil mode, or In dual-foil mode, detected resistance either above RMAX or below RMIN, or In dual-foil mode, the detected resistance having risen by more than a predetermined percentage above the resistance present when the user last pressed set point switch S2, or In dual-foil mode, detected resistance within the allowed range, but not having been registered as valid by the user having activated S2 since the later of:
  selection of dual-foil mode, or
  detection plate fault producing an alarm output.

Once a dual foil alarm has been declared, it will remain active until the resistance returns to within the allowable range and the set point is re-established by the user.

Figure 8:
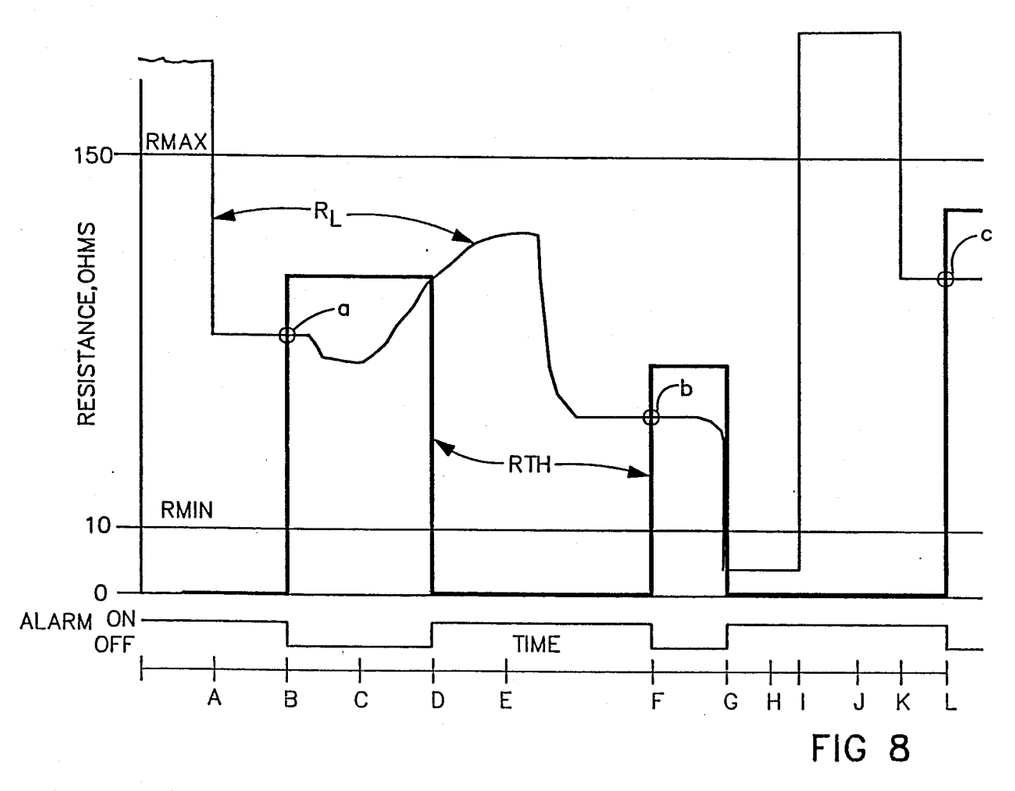
FIG. 8 is a graph showing the relationship of resistance at the return part of the patient circuit and a variety of operational events together with the associated on-off positions for the alarm.

The functions performed by the microprocessor may be further understood with reference to a sequence of events shown in FIG. 8 wherein the events are listed as follows:

Event

A. Pad placed on patient and resistance is between RMAX and RMIN values.
B. Set point switch S2 activated establishing first RTH limits at point a.
C. Pad pulls loose gradually causing the resistance to increase.
D. Resistance rises above threshold RTH, alarm goes on, and RF power source is inhibited.
E. Pad contact restored by user OR staff.
F. Set point switch S2 activated again to establish new RTH limits at point b.
G. Pad shorts out dropping resistance below RMIN.
H Set point switch S2 activated—alarm continues since resistance is less than RMIN.
I. Remove defective pad causing resistance to exceed RMAX.
J. Set point switch S2 activation attempted—still rejected since resistance is greater than RMAX.
K. Connect and attach new pad to patient.
L. Activate set point switch S2 establishing new RTH limits at point c.

By way of illustration only and not by way of limitation, there are listed below devices which have been found suitable for use in the illustrated circuits.

| Reference No. | Part No. | |
|---|---|---|
| U1 | LM317L | NATL. SEMICONDUCTOR |
| U2 | LM358 | NATL. SEMICONDUCTOR |
| U4 | LM339 | NATL. SEMICONDUCTOR |
| U3 | AD558 | ANALOG DEVICES |
| 23 | 8031 | INTEL |

The Q above described is greater than 200 at 40 KHz. KT referred to in FIG. 6 is a threshold constant where RTH=KT×RL. A preselected fixed deviation of the resistance value determined by the set point means of 20 to 30% has been shown to reliably indicate pad detachment prior to an unsafe degree of contact being established. In this case KT=1.2 to 1.3.

It is understood that a single transformer could be used for the oscillator and isolation and a potentiometer could be used for the set point switch as a set point means. Vacuum tubes could be used in place of the transistors. Moreover a circuit could provide current instead of voltage as a measure of the resistance. This could be voltage fed and the DC supply current measured.

Although the present invention has been described with a certain degree of particularity, it is understood that the present disclosure has been made by way of example and that changes in details of structure may be made without departing from the spirit thereof.

What is claimed is:

1. A return electrode contact monitor for electrosurgical apparatus including a RF power source coupled to an active electrode and a patient circuit including a return electrode for operative association with a patient, said monitor comprising:
   first means for producing an electric signal that varies with the resistance of a return part of the patient circuit, and
   circuit means responsive to said electric signal, said circuit means establishing a preselected resistance value range beyond which an alarm output is produced, a manually operable set point actuator means, said circuit means including set point means responsive to said actuator means providing a threshold corresponding to the resistance at the last time said actuator means was actuated whereby upon a preselected fixed deviation of said resistance from said threshold and within said range an alarm output is produced.

2. A return electrode contact monitor as set forth in claim 1 wherein said electric signal is a substantially DC voltage.

3. A return electrode contact monitor as set forth in claim 2 wherein said circuit means includes an analog to digital converter to convert said substantially DC voltage to a corresponding binary digital signal.

4. A return electrode contact monitor as set forth in claim 3 wherein said circuit means includes a programmed microprocessor that receives said binary digital signal.

5. A return electrode contact monitor as set forth in claim 1 wherein said first means includes a DC to AC converter having an AC output and a DC input, said resistance of a return part of the patient circuit being applied to said AC output, said converter providing a DC resistance at said DC input that varies substantially in relation to said resistance at said AC output.

6. A return electrode contact monitor as set forth in claim 5 wherein said DC to AC converter includes push-pull sine wave oscillator.

7. A return electrode contact monitor as set forth in claim 6 including a substantially constant current source supplying power to said sine wave oscillator.

8. A return electrode contact monitor as set forth in claim 6 including a low pass filter through which the output voltage of the oscillator is passed so the voltage will more nearly appear as DC.

9. A return electrode contact monitor as set forth in claim 6 wherein said oscillator includes a transformer coupled to first and second transistors which transformer has a relatively high Q.

10. A return electrode contact monitor as set forth in claim 6 including a transformer between said return electrode and oscillator to isolate the oscillator from high RF voltages which may appear in the patient circuit.

11. A return electrode contact monitor as set forth in claim 5 wherein said converter has a DC input voltage and a DC input current, said DC input voltage of the converter varying in a substantially logarithmic relationship with the return resistance of the patient circuit when said DC input current of the converter is constant.

12. A return electrode contact monitor as set forth in claim 1 wherein said first means includes a DC to AC converter having a DC input and an AC output with said patient circuit being coupled to the AC output, said converter providing a DC input current that varies in relation to AC output current and a DC input voltage that varies in relation to AC output voltage, said DC input voltage being used as said electric signal.

13. A return electrode contact monitor as set forth in claim 1 wherein said circuit means provides a further output to turn off the RF power source each time an alarm is produced.

14. A return electrode contact monitor as set forth in claim 1 including dual foil select switch means coupled to said circuit means to set the operation for a dual foil return electrode in said patient circuit.

15. A return electrode contact monitor as set forth in claim 1 including single foil select switch means coupled to said circuit means to set the operation for a single foil return electrode in said patient circuit.

16. A return electrode contact monitor as set forth in claim 1 including a visual indicator coupled to said circuit means for indicating the value of said resistance each time a set point actuator means is actuated.

17. A return electrode contact monitor for electrosurgical apparatus including a RF power source coupled to an active electrode and a patient circuit providing a return load resistance including a return electrode for operative association with a patient, said monitor comprising:
   detector means including a DC to AC converter in the form of a current fed push-pull sine wave oscillator and a low pass filter for producing a substantially DC voltage related to the resistance of the return part of the patient circuit, and
   circuit means including an analog to digital converter and a programmed microprocessor, said converter converting said substantially DC voltage to a corresponding binary digital signal that is input to said microprocessor, a manually operable set point switch coupled to said microprocessor, said microprocessor establishing preselected fixed maximum and minimum resistance value limits beyond which an alarm output is produced and said microprocessor further including set point means providing a threshold corresponding to the resistance at the instant of the last set point switch activation whereby upon a preselected fixed deviation of said resistance above said threshold and within said maximum and minimum value limits an alarm output is produced, said microprocessor providing an output to shut off the RF power source each time an alarm output is produced.

* * * * *

REEXAMINATION CERTIFICATE (2311th)
United States Patent [19]
Manes

[11] B1 4,848,335
[45] Certificate Issued   Jun. 7, 1994

[54] RETURN ELECTRODE CONTACT MONITOR

[75] Inventor: Michael R. Manes, Littleton, Colo.

[73] Assignee: Aspen Laboratories, Inc., Greenwood Village, Colo.

Reexamination Request:
No. 90/003,034, Apr. 15, 1993

Reexamination Certificate for:
Patent No.: 4,848,335
Issued: Jul. 18, 1989
Appl. No.: 156,540
Filed: Feb. 16, 1988

[51] Int. Cl.⁵ ............................................. A61B 17/39
[52] U.S. Cl. ..................................... 606/35; 128/908
[58] Field of Search ................... 606/35, 32; 128/908

[56] References Cited
U.S. PATENT DOCUMENTS

3,933,157  1/1976  Bjurwill .
4,200,104  4/1980  Harris .
4,303,073  12/1981  Archibald .
4,416,276  11/1983  Newton .
4,416,277  11/1983  Newton .

FOREIGN PATENT DOCUMENTS
1139927  11/1962  Fed. Rep. of Germany .

*Primary Examiner*—Lee S. Cohen

[57] ABSTRACT

Apparatus for monitoring the resistance of the return part of the patient circuit of either a dual foil or single foil return electrode according to the user's selection is disclosed. The apparatus measures the quality of the contact between the return electrode and the patient. A DC or AC converter provides a substantially DC voltage at its input that varies in relation to the resistance of the return part of the patient circuit at its AC output. Preferably, a constant current fed sinusoidal oscillator with a low pass filter at its DC output provides a substantially DC voltage related to the resistance at its AC input. An analog to digital converter converts the substantially DC voltage to a corresponding binary digital signal that is input to a programmed microprocessor. A manually operable set point switch coupled to the microprocessor is acatuated by the user which actuation establishes a resistance level with the pad (return electrode) in place on the patient. The microprocessor establishes preselected range between fixed maximum and minimum resistance values beyond which an alarm output is produced and establishes a threshold resistance value whereby upon a preselected fixed deviation, such as when the patient pad is partially detached, an alarm is produced and further an output so the RF power source will longer apply power to the active electrode.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-17 is confirmed.

* * * * *